Figure 1:
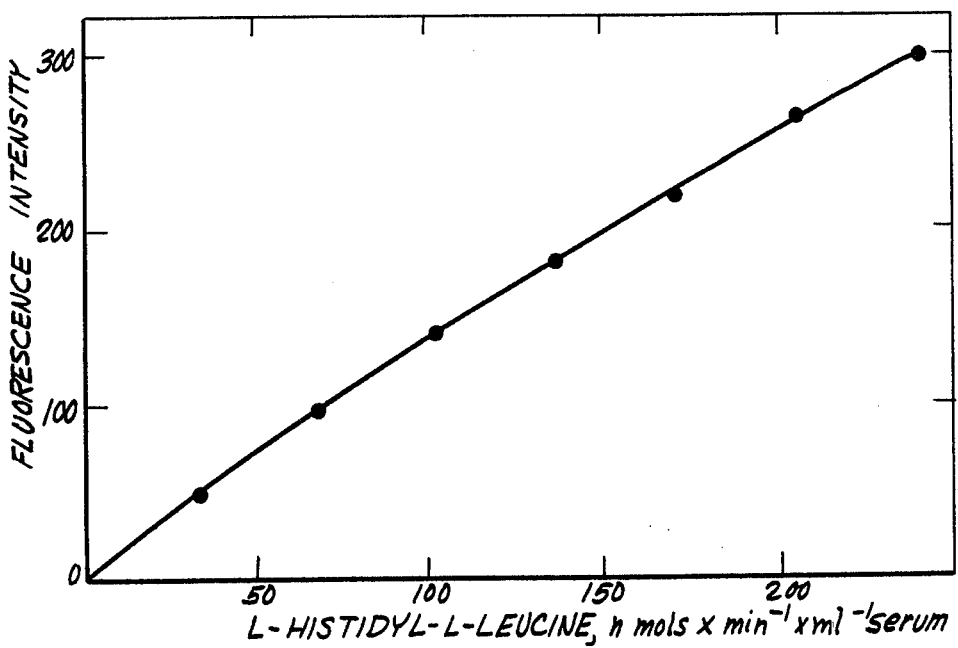

United States Patent [19]

Silverstein

[11] 4,108,726

[45] Aug. 22, 1978

[54] SARCOIDOSIS TEST

[75] Inventor: Emanuel Silverstein, Brooklyn, N.Y.

[73] Assignee: Research Corporation, New York, N.Y.

[21] Appl. No.: 705,432

[22] Filed: Jul. 15, 1976

[51] Int. Cl.² ........................................... G01N 31/14
[52] U.S. Cl. .................................. 195/103.5 R; 424/7
[58] Field of Search ............... 195/103.5 R, 99; 424/7

[56] References Cited

PUBLICATIONS

Piquilloud, et al., Studies on the Angiotensin Converting Enzyme with Different Substrates, Biochimica et Biophysica Acta, vol. 206, 1970 (pp. 136–142).

Cheung et al., Inhibition of Homogeneous Angiotensin-Converting Enzyme of Rabbit Lung by Synthetic Venom Peptides of Bothrops Jararaca, Biochimica et Biophysica Acta, vol. 293, 1973 (pp. 451–463).

*Primary Examiner*—David M. Naff
*Attorney, Agent, or Firm*—Cooper, Dunham, Clark, Griffin & Moran

[57] ABSTRACT

Serum angiotensin converting enzyme is elevated in many patients with sarcoidosis. A method involving formation of the fluorescent adduct of o-phthaldialdehyde and the histidyl moiety of the L-histidyl-L-leucine product formed by the action of angiotensin converting enzyme on hippuryl-L-histidyl-L-leucine substrate is applicable to determining angiotensin converting enzyme in untreated serum for the diagnosis of sarcoidosis. This method is simple, rapid and highly sensitive, and requires as little as one ul or less of a serum.

8 Claims, 5 Drawing Figures

SARCOIDOSIS TEST

This invention relates to serum angiotensin converting enzyme. Serum angiotensin converting enzyme has been observed to be elevated in many patients with sarcoidosis, see Lieberman, J. (1974) A new confirmatory test for sarcoidosis. Serum angiotensin converting enzyme. Effect of steriods and chronic lung disease. *Amer. Rev. Resp. Dis.* 109, 743 (1974); Silverstein, E., Friedland, J., Lyons, H. and Kitt, M. Serum angiotensin converting enzyme in sarcoidosis. *Clin. Res.* 23, 352A; Silverstein, E., Friedland, J., Lyons, H. and Gourin, A. Elevated angiotensin converting enzyme activity in non-necrotizing granulomatous lymph nodes in sarcoidosis. *Clin. Res.* 23, 352A.

Angiotensin-converting enzyme, see Skeggs, L. T., Marsh, W. H., Kahn, V. R. and Shumway, N. P. (1954) *J. Exp. Med.* 99, 275, is a halide requiring dipeptidase which catalyzes the cleavage of the carboxyl end of the decapeptide angiotensin I to form the pressor octapeptide angiotensin II and the dipeptide L-histidyl-L-leucine, see Bakhle, Y. S. (1974) Converting enzyme in vitro measurements and properties. *Handbook of Exper. Pharm.* 37, 41–80; Erdos, E. G. (1975) Angiotensin I converting enzyme. *Circ. Res.* 36, 247–255:

asp-arg-val-tyr-ile-his-pro-phe-his-leu ⟶ (angiotensin I)

asp-arg-val-tyr-ile-his-pro-phe + his-leu. (angiotensin II)

The substrate, angiotensin I, is itself formed by proteolytic cleavage from the serum protein precursor angiotensinogen catalyzed by the enzyme renin which is present in juxtaglomerular cells of the kidney and released in a controlled manner from them. Angiotensin converting enzyme is an important element in the renin-angiotensin system of blood pressure and aldosterone control, see Davis, J. O. (1973). The control of renin release. *Am. J. Med.*, 55, 333, as in neural action, see Daul, C. B., Heath, R. G. and Garey, R. E. (1975). Angiotensin-forming enzyme in human brain. *Neuropharmacology*, 14, 75–80. In addition to plasma, angiotensin converting enzyme is present in various organs, particularly in lung, see Cushman, D. W. and Cheung, H. S. (1971). Concentration of angiotensin-converting enzyme in tissues of the rat. *Biochem. Biophys. Acta*, 250, 261–265, the organ which appears to be responsible for much of the rapid conversion in vivo of angiotensin I to angiotensin II, see NG, K.K.F., Van, V. R. (1968). Fate of angiotensin I in the circulation, *Nature* (Lond) 218, 144–150.

Angiotensin converting enzyme has been assayed with angiotensin I as substrate biologically by contractile, see Helmer, O. M. (1957) Differentiation between two forms of angiotonin by means of spirally cut strips of rabbit aorta. *Am. J. Physiol.* 188, 571–; Huggins, C. G., Corcoran, R. J., Gordon, J. S., Henry, H. W., John, J. P. (1970). Kinetics of the plasma and lung angiotensin I converting enzymes. *Circ. Res.* 26–27, *Suppl. I.* 93–101; Andersen, J. B. (1967). Converting enzyme activity in liver damage. *Acta Path. Microbiol. Scand.* 71, 1; Barrett, J. D., Sambhi, M. P. (1969). Simultaneous assay of angiotensin I and II and determination of converting enzyme activity. *J. Pharmacol. Exp. Ther.* 170, 326; Ueda, E., Akutsu, H., Kokubi, T., Yamamura, Y. (1971). (1) Partial purification and properties of angiotensin I converting enzyme from rabbit plasma. *Jap. Circ. J.* 35, 801; Bakhle, Y. S. (1968) Conversions of angiotensin I to angiotensin II by cell-free extracts of dog lung. *Nature* (Lond) 220, 919–, or blood pressure, see Loyke, H. F. (1970) Converting enzyme in rat serum. *Proc. Soc. Exp. Biol. Med.* 134, 248, response, radiometrically by measuring the release in histidyl-leucine of radioactivity in the terminal leucine in angiotensin I, see Huggins, C. G., Thampi, N. S. (1968) A simple method for the determination of angiotensin I converting enzyme. *Life Sci.* 7, 633, spectrofluorimetrically, see Piquilloud, Y., Reinharz, A., Roth, M. (1970) Studies on angiotensin converting enzyme with different substrates. *Biochem. Biophys. Acta.* 206, 136–142; Cheung, H. S. and Cushman, D. W. (1973). Inhibition of homogenous angiotensin converting enzyme of rabbit lung by synthetic venom peptides of *Bothrops Jararaca*. *Biochim et Biophy. Acta.* 293, 450–463, spectrophotometrically by ninhydrin reaction, see Dorer, F. E., Skeggs, L. T., Kahn, J. R., Lentz, K. E., Levine, M. (1970). Angiotensin converting enzyme. Method of assay and partial purification. *Analyt. Biochem.* 33, 102, and by separation of product and precursor by countercurrent distribution, see Skeggs, L. T., Kahn, J. R., Shumway, N. P. (1956). Purification of hypertensin II. *J. Exp. Med.* 103, 301. Simpler substrate analogues have been assayed similarly with the exception of biological activity since no such activity is generated with the analogues, see Piquilloud, Y., Reinharz, A., Roth, M. (1970). Studies on angiotensin converting enzyme with different substrates. *Biochem. Biophys. Acta.* 206, 136–142; Cushman, D. W., Cheung, H. S. (1971). Spectrophotometric assay and properties of the angiotensin converting enzyme of rabbit lung. *Biochem. Pharmacol.* 20, 1673; Yang, H. Y. T., Erdos, E. G., Levin, Y. (1971). Characterization of a dipeptide hydrolase (Kininase II: angiotensin I converting enzyme). *J. Pharmacol. Exp. Ther.* 177, 291, (1971); Elisseeva, Y. E., Orekhovich, V. N. (1964). Isolation of carboxycathepsin and examination of its specificity. *Dokl. Akad. Nauk.* SSSR, 153, 1434; Igic, R., Erdos, E. G., Yeh, H. S. J., Sorrells, K., Nakajima, T. (1972). The angiotensin I converting enzyme of the lung. *Circ. Res.* 31, *Suppl. II*, 51.

Partially purified human plasma or serum angiotensin-converting enzyme has been determined radiometrically with [$^{14}$C-leu]-5-ile-angiotensin I as substrate, see Lee, H. J., Larue, V. N., Wilson, I. B. (1971). *Arch. Biochem. Biophys.*, 142, 548–551, and fluorimetrically with angiotensin I or benzyloxycarbonyl-phe-his-leu or benzyloxycarbonyl-pro-phe-his-leu, see Piquilloud, Y., Reinharz, A., Roth, M. (1970). Studies on angiotensin converting enzyme with different substrates. *Biochem. Biophys. Acta.* 206, 136–142, while purified or unpurified human plasma was assayed with angiotensin I substrate biologically, see Boucher, R., Kurihara, H., Grise, C., Genest, J. (1970). *Circ. Res.*, 26–27, *Suppl. I*, 83–91; Fitz, A., Boyd, G. W., Peart, W. S. (1971). Converting enzyme activity in human plasma. *Circ. Res.*, 28, 246–253, or radioimmunologicaly, see Fitz, A., Boyd, G. W., Peart, W. S. (1971). Converting enzyme activity in human plasma. *Circ. Res.*, 28, 246–253.

In terms of a clinically applicable serum assay, the spectrophotometric assay utilizing hippuryl-L-histidyl-L-leucine substrate, see Cushman, D. W. and Cheung, H. S. (1971). Spectrophotometric assay and properties of angiotensin converting enzyme of rabbit lung. *Biochem. Pharmacol.* 20, 1637–1648, was not applicable to sera containing significantly high levels of lipids since they interfered with the extraction and subsequent solubilization of the product hippuric acid. This assay also required fastidious technique and was relatively insensitive. The spectrofluorimetric method of this invention is a modification of a method previously described which was unsuitable for assay of unpurified serum angiotensin converting enzyme.

An object of this invention is to provide a method or technique for the diagnosis of sarcoidosis and the like.

Figure 2:
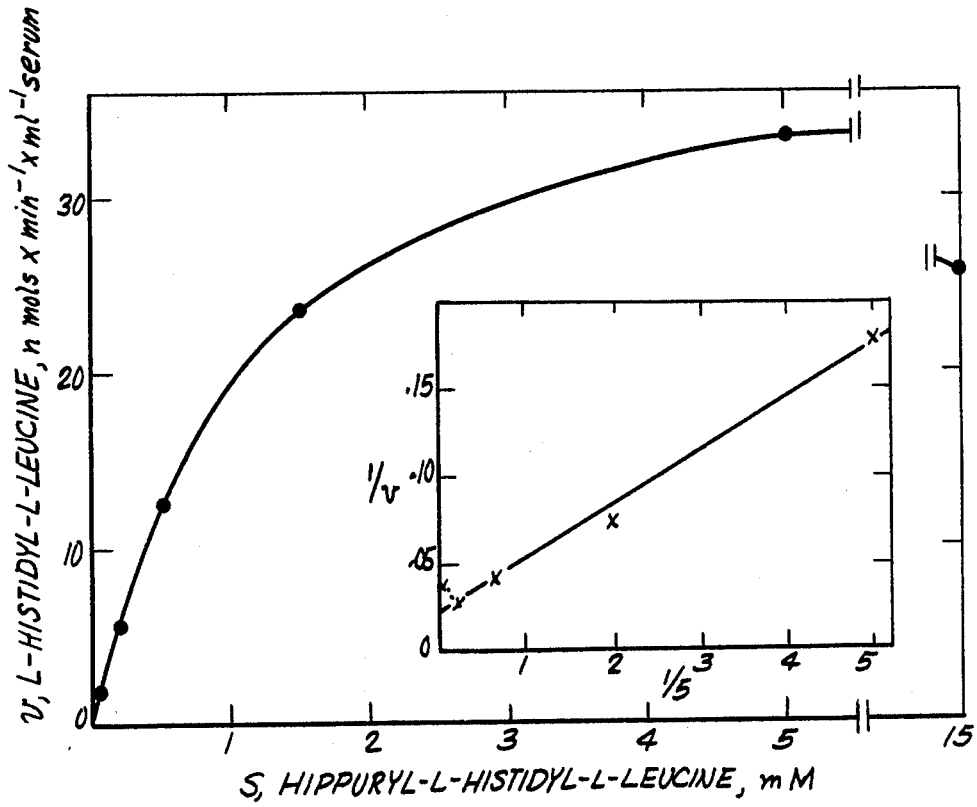
Figure 3:
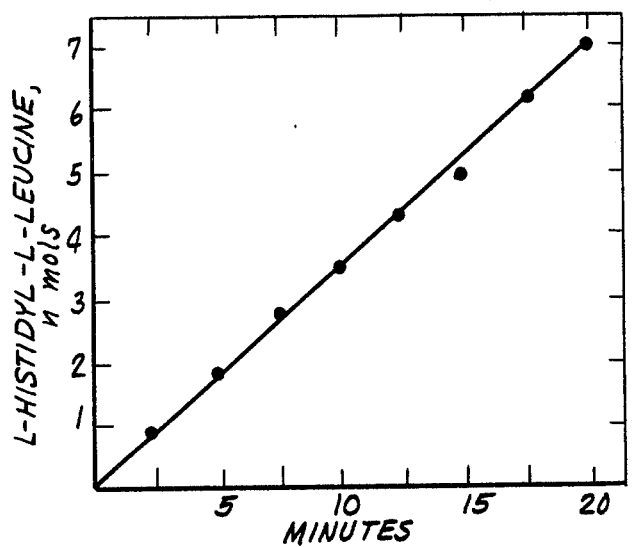
Figure 4:
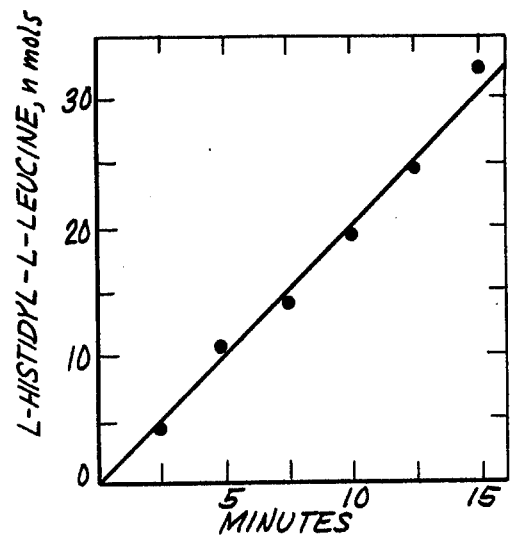
Figure 5:
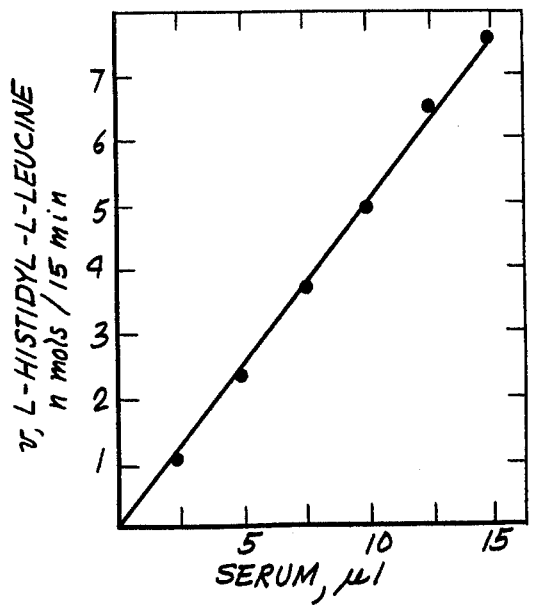

How this and other objects of this invention are achieved will become apparent from the accompanying disclosure and drawings wherein FIG. 1 is the standard curve of L-histidyl-L-leucine quantity versus fluorescence intensity. The units of L-histidyl-L-leucine are given directly in terms of velocity/ml serum in the standard assay as described in Expermental Procedure. The actual L-histidyl-L-leucine concentration in nmols/ml may be obtained by multiplying by 0.6;

FIG. 2 is a graphical representation of the velocity of formation of L-histidyl-L-leucine catalyzed by serum angiotensin-converting enzyme as a function of the concentration of the substrate, hippuryl-L-histidyl-L-leucine. The serum used had an activity of 30 nmol/min/ml serum;

FIG. 3 graphically represents the linearity with respect to time of the formation of L-histidyl-L-leucine from hippuryl-L-histidyl-L-leucine catalyzed by serum angiotensin-converting enzyme (activity, 30 nmol/min/ml serum);

FIG. 4 graphically represents the linearity with respect to time of the formation of L-histidyl-L-leucine catalyzed by a high activity of serum angiotensin-converting enzyme from a patient with sarcoidosis; and FIG. 5 graphically represents the linearity with respect to serum concentration of the velocity of L-histidyl-L-leucine formation catalyzed by serum angiotensin-converting enzyme. The reaction mixture contained 0.5M NaCl, 0.1 K phosphate, pH 8.3, 5mM hippuryl-L-histidyl-L-leucine, and enzyme as noted in the figure in 0.25 ml. Standards and blanks were prepared for each serum concentration to control any influence of serum on fluorescence intensity. Serum quantities below 10 $\mu$l were obtained by using serum diluted 1/10 with saline solution.

The practice of this invention is based on formation of the fluorescent adduct of o-phthaldialdehyde and the histidyl moiety of the L-histidyl-L-leucine product, see Piquilloud, Y., Reinharz, A., Roth, M. (1970). Studies on angiotensin converting enzyme with different substrates. *Biochem. Biophys. Acta.* 206, 136–142; Shore, P. A., Burkhalter, A., Cohn, V. H., Jr. (1959). A method for the fluorimetric assay of histamine in tissues. *J. Pharm. Exp. Ther.* 127, 182; Gregerman, R. I. (1967). Identification of histidyleucine and other histidyl peptides as normal constituents of human urine. *Biochem. Med.* 1, 151–167, formed from the hippuryl-L-histidyl-L-leucine substrate. This invention is applicable to untreated sera, simple, rapid, and highly sensitive, requiring as little as 1 $\mu$l or less of serum and has been applied to the study of large numbers of sera in sarcoidosis, see Silverstein, E., Friedland, J., Lyons, H. and Kitt, M. Serum angiotensin converting enzyme in sarcoidosis. *Clin. Res.* 23, 352A.

EXPERIMENTAL PROCEDURE

Materials

Hippuryl-L-histidyl-L-leucine, L-histidyl-L-leucine, o-phthaldialdehyde, methanol and various inorganic chemicals.

Serum Samples

Blood was obtained from healthy donors (unless otherwise noted) by arm venipuncture. The blood was allowed to clot in a new clean test tube for about an hour at room temperature, centrifuged for 10 minutes at 900 g and the serum carefully removed with a Pasteur pipette and stored at $-76°$ to $-86°$ C.

Reagents

Distilled and deionized water was used throughout. Hippuryl-L-histidyl-L-leucine (25mM, pH 8.3, molecular weight 466) was prepared by dissolving 46.6 mg hippuryl-L-histidyl-L-leucine in 4 ml of 25mM NaOH.

Phospho-saline buffer (pH 8.3) was prepared by dissolving 87.09 g (0.5 mole) $K_2HPO_4$ and 87.67 g (1.5 mole) NaCl in 900 ml $H_2O$, adjusting the pH to 8.3 with 1N HCl, adding water to a total volume of 1 l and readjusting the pH if necessary. This buffer keeps well at room temperature but precipitates at 5° C.

Substrate-buffer solution was prepared by mixing buffer, substrate and water at a ratio of 1:1:2.8 (final concentration in the assay mixture; 0.1M K phosphate, pH 8.3, 0.3M NaCl; 5mM hippuryl-L-histidyl-L-leucine).

Two % o-phthaldialdehyde (200 mg/10 ml purified methanol) was prepared immediately prior to addition of enzyme to a series of assay mixtures.

A product standard consisted of 0.2 ml 0.516 mM L-histidyl-L-leucine (13.86 mg/100 ml $H_2O$), 1 ml buffer and 3.6 ml $H_2O$; 0.24 ml of standard solution contained 5.16 nmol L-histidyl-L-leucine. Dilutions of the standard were used for establishing the standard curve. Serum was added to the standard after addition of 0.28 N NaOH to eliminate any possible error from enzymatic hydrolysis of L-histidyl-L-leucine. Since the variation among standards containing different sera was less than 5%, usually 3 of the series being assayed were added to the standard and the mean value of fluorescence intensity obtained was used to correlate fluorescence with the content of the reaction product, L-histidyl-L-leucine. The fluorescence of a blank containing water and serum was substracted from that of the standard and serum.

Enzyme Incubation

Ten $\mu$l of serum was added to 240 $\mu$l of substrate-buffer solution at 37° C. in a 12 $\times$ 75 mm test tube tightly covered with Parafilm, mixed with a vortex mixer and incubated for 15 minutes at 37° C. Duplicate reaction mixtures were stopped by addition of 1.45 ml of 0.28 M NaOH and mixing with a vortex mixer. A substrate-buffer blank was similarly treated at the same time except that enzyme was added immediately after NaOH, and was an important control for the slow breakdown of hippuryl-L-histidine-L-leucine in NaOH. In order to keep the blank low, the development of fluorescence should be started as soon as possible after the addition of NaOH.

Fluorescent Product Development

One hundred μl of o-phthaldialdehyde reagent was added to each tube which was mixed with a vortex mixer. Exactly 10 minutes later the reaction was terminated by the addition of 200 μl of 3 M HCl and the tube again thoroughly mixed. The HCl addition is accompanied by the precipitation of a presumptive protein-o-phthaldialdehyde complex which was removed by centrifugation for 10 minutes at 1000 g. The fluorescence was read in a 1 cm rectangular fluorescence cuvette in a Perkin-Elmer MPF-4 fluorimeter with 8 mm entrance and exit slits and a 7.5 V energy output between 30 and 90 minutes after addition of HCl, during which time it was stable. The excitation wavelength was 360 nm and the emission fluorescence wavelength was 500 nm.

Calculations

Enzyme activity in nmoles L-histidyl-L-leucine/min/ml serum was calculated by two methods. The first is applicable for ratios of up to 2 of corrected assay/standard fluorescence. The second method must be used for ratios greater than 2 and is applicable to ratios below 2 as well.

Method 1

Angiotensin converting enzyme activity, nmol his-leu/min/ml serum =

$$\frac{5.166 \text{ nmol his-leu (standard) } 100 \text{ ml}^{-1} \text{ serum (FI assay } - \text{ FI assay blank)}}{15 \text{ min (FI standard } - \text{ FI standard blank)}}$$

Method 2

A standard curve of (standard-blank) fluorescence versus L-histidyl-L-leucine was prepared by using integral multiples of the routine standard up to seven under the same condition as for the routine standard, see FIG. 1. The quantity of L-histidyl-L-leucine in nmoles/0.01 ml serum in each standard was converted to nmol/min/ml of serum by multiplying by 100/15 minutes. Enzyme activity was read from the standard curve using the fluorescence obtained in the assay corrected for fluorimeter variation by multiplying by fluorescence of standard when the curve was made/fluorescence of standard at the time of assay.

Hydrolysis of L-histidyl-L-leucine

Hydrolysis of the product L-histidyl-L-leucine was determined fluorimetrically by adding L-histidyl-L-leucine to an assay mixture which contained buffer and serum and was handled as described for the enzyme assays, including a zero time control. Hydrolysis was accompanied by a decrease in fluorescence from that obtained with the initial concentration as determined in the zero time control. The quantity hydrolyzed was determined by multiplying the fraction hydrolyzed (decrease in FI/initial FI) by the initial concentration. No correction was made for the fluorescence of L-histidine since it was only about 8% of the fluorescence of L-histidyl-L-leucine.

Results

Initial Assay Development

Initially the method of Cheung and Cushman, see Cheung, H. S., Cushman, D. W. inhibition of homogeneous angiotensin converting enzyme of rabbit lung by synthetic venom peptides of *Bothrops jararaca Biochem. Biphys. Acta* 293, 451–463, (1973), was tried to assay fluorimetrically for angiotensin converting enzyme in serum, but was unsuccessful. Essentially no fluorescence was obtained apparently because o-phthaldialdehyde also reacts with the abundant serum proteins leaving insufficient reagent to react with the L-histidyl-L-leucine product formed from hippuryl-L-histidyl-L-leucine. By increasing the o-phthaldialdehye concentration from 0.2 to 2%, there was sufficient reagent to form the fluorescent L-histidyl-L-leucine adduct. Under these conditions, the fluorescence intensity of L-histidyl-L-leucine in buffer in the presence of serum was 80% of that obtained in the absence of serum. Even at a serum content of 10 μl instead of 50 μl, a concentration of o-phthaldialdehyde of greater than 0.2% was required since the fluorescence intensity with 0.2 % o-phthaldialdehyde was only 62% of that with 2% o-phthaldialdehyde. The results indicated the importance of controlling for the effect of serum per se on the fluorescence intensity.

This early assay procedure (half the volume of Cheung and Cushman, see Cheung, H. S. and Cushman, D. W. (1973). Inhibition of homogenous angiotensin converting enzyme of rabbit lung by synthetic venom peptides of *Bothrops jararaca. Biochim. et Biophy. Acta* 293, 451–463,: 0.125 ml total reaction volume, 0.05 ml serum; 2% o-phthaldialdehyde) had two drawbacks. First, the assay was not linear and, second, human serum was found to contain a peptidase which hydrolyzes L-histidyl-L-leucine. Since the o-phthaldialdehyde-histidine addition product was found to have a quantum yield of about 8% that of the o-phthaldialdehyde-L-histidyl-L-leucine addition product, the activity measured would be lower than the true activity by almost the entire amount of the L-histidyl-L-leucine hydrolyzed.

L-histidyl-L-leucine Peptidase

The activity of the L-histidyl-L-leucine hydrolyzing activity was measured in several sera under the conditions of the orginal assay (50 μl sera in 125 μl 0.1 M K phosphate-0.3 M NaCl, pH 8.3) using as substrate 0.2 mM L-histidyl-L-leucine, a concentration typically formed in the angiotensin converting enzyme reaction mixture. This measurement indicated that an underestimation of up to 15% might be introduced in the assay of angiotensin converting enzyme in this system. The velocity of the L-histidyl-L-leucine peptidase reaction was determined at varying L-histidyl-L-leucine concentrations. The Km for L-histidyl-L-leucine of the peptidase was estimated from 1/v-1/S plots, see Lineweaver, H. and Burk, D. (1934). *J. Amer. Chem. Soc.* 56, 658, to be 0.16 mM. This is similar to the value of 0.2 mM for the Km of porcine lung L-histidyl-L-leucine peptidase, see Lee, H. J., Larue, J. N. and Wilson, I. B. (1971). Angiotensin converting enzyme from guinea pig and hog lung. *Biochim. Biophys. Acta.* 250, 549. Reduction of the volume of serum used to 10 μl and increase in total reaction volume to 250 μl would reduce the concentration of the L-histidyl-L-leucine product ten-fold. The angiotensin converting enzyme activity of most human sera (32 nmol/min/ml serum; 0.02 mM L-histidyl-L-leucine formed in 15 minutes) would result in a L-histidyl- L-leucine concentration well below the Km for L-histidyl-L-leucine of its peptidase activity. From the rates of hydrolysis of 0.02 mM L-histidyl-L-leucine in 250 μl assays using 10 μl of serum from several patients, it was estimated that less than 2.5% of the L-histidyl-L-leucine formed would be likely to be hydrolyzed in the new assay system. Therefore, essentially no correction would be required for hydrolysis of L-histidyl-L-leucine.

Apparent Hydrolysis of Hippuryl-L-histidyl-L-leucine in NaOH

The fluorescence intensity of the zero time blank containing NaOH and enzyme increased linarly with the time elapsed between NaOH addition and fluorescence development with o-phthaldialdehyde, suggesting a slow base-catalyzed hydrolysis of hippuryl-L-histidyl-L-leucine to hippurate and L-histidyl-L-leucine. When large quantities of enzyme were used, this effect was small compared to the total fluorescence developed. However, the increase in fluorescence intensity of the blank in 30 minutes was equivalent to 1.3 nmol/min/ml and would result in a value 4% below the true one for an enzyme activity of 34 nmol/min/ml, which is in the normal range. To avoid spuriously high blanks due to base catalyzed hydrolysis, addition of NaOH to the blank, followed by enzyme, was made at the same time that NaOH was added to terminate the enzymatic reaction of the reacted samples.

Kinetics

The effect of substrate concentration on reaction velocity is given in FIG. 2. Maximum activity was noted at 5 mM hippuryl-L-histidyl-L-leucine and inhibition at 15 mM. The Km determined from the 1/v-1/S plot, see Lineweaver, H., Burk, D. The determination of enzyme dissociation constants. *J. Am. Chem. Soc.* 56, 658 (1934), was 1.33 mM. Five mM hippuryl-L-histidyl-L-leucine was selected as close to optimum for the standard assay. This concentration of substrate was also used for the rabbit lung enzyme system in which, similarly, the Km was 2.6 mM and inhibition was present above 10 mM substrate, see Cushman, D. W., Cheung, H. S. Spectrophotometric assay and properties of the angiotensin converting enzyme of rabbit lung. *Biochem. Pharmacol.* 20, 1637 (1971).

Initial rate conditions were present and a linear release of product with time would be expected since assay of serum of the highest activity (240 nmol/min/ml serum) resulted in utilization of less than 3% of the substrate during 15 minute assay. The formation of the product, L-histidyl-L-leucine, was linear with time for serum, both of normal activity, see FIG. 3, and markedly elevated activity from a patient with sarcoidosis, see FIG. 4. The velocity of the reaction was directly proportional to the concentration of serum enzyme added, indicating that the assay measures the amount of enzyme present and is valid, see FIG. 5.

Normal Values

The mean serum angiotensin converting enzyme in 58 healthy blood bank donors (51 male, 19–57 years of age, means age, 31.6 years; 7 female, 21–44 years old, mean age, 33.3 years) was 32.2 ± 1.30 (standard error of the mean) ± 9.87 (standard deviation) nmol/min/ml serum. The values of two individuals were between two and three standard deviations greater than the mean, and one was greater than three standard deviations. There were no values more than two standard deviations below the mean.

The fluorescent assay of this invention for serum angiotensin converting enzyme activity has several advantages in comparison to the spectrophotometric method. It is applicable to sera drawn at any time and is extremely sensitive. The present assay could be run on as little as 1 μl of serum by lengthening incubation time if necessary or increasing the sensitivity range of the fluorimeter if possible on the instrument available. Further increase in sensitivity could be obtained by a decrease in the size of the incubation mixture and use of microcuvettes. The method of this invention is on a micro level and almost any size of sample can be assayed. This is important where sample size is limited, as in pediatrics, where multiple determinations are required, and for micro sampling studies. In contrast, the spectrophotometric assay requires 100 μl of serum and a 30 minute incubation time in the normal range. The subject fluorescent assay can be run on large numbers of serum at a time, and is rapid and relatively simple to perform.

The angiotensin converting enzyme assay herein described appears to be useful for diagnosis and management of patients with sarcoidosis who may have extremely elevated levels, see Silverstein, E., Friedland, J., Lyons, H., Kitt, M. Serum angiotensin converting enzyme activity in sarcoidosis *Clin. Res.* 23, 352A (1975); Lieberman, J. A new confirmatory test for sarcoidosis. Serum angiotensin converting enzyme. Effect of chronic lung disease. *Am. Rev. Resp. Dis.* 109, 743 (1974); Lieberman, *J. Am. J. Med.* 59 365 (1975). and may in the future have other clinical uses as well.

Angiotensin converting enzyme activity in serum has been found to be elevated in new-born infants with idiopathic respiratory distress syndrom, see Mattioli, L. et al. *J. Pediatrics* 87, 97–101 (July 1975). Thus, the subject assay would have use in new-born infants where its high sensitivity and accuracy would make it ideal for use with limited sample. The subject invention or assay would also be useful in the diagnosis of the genetic disease known as Gaucher's Disease. Further, the subject invention is readily adaptable to automation.

Although emphasis in the practice of this invention is based on the conversion of the substrate analogue, hippuryl-L-histidyl-L-leucine to hippurate and L-histidyl-L-leucine which is quantified spectrofluorimetrically by formation of a fluorescent adduct with o-phthaldialdehyde, in the practice of this invention angiotensin I is also useful as a substrate. Angiotensin I as a substrate in the practice of this invention, however, is more expensive and its activity considerably lower. For routine clinical use, it is believed the preferred substrate in the practice of this invention will be hippuryl-L-histidyl-L-leucine. When angiotensin I is employed as the substrate, the following procedure would be employed in accordance with this invention for the measurement of serum angiotensin converting enzyme activity.

Three mg of angiotensin I were dissolved in 10 ml buffer, 0.03125 M NaCl and 0.104 M potassium phosphate, pH 7.5. The optical density (O.D.) of the solution at 275 nM was measured against the buffer. The O.D. of the angiotensin I solution was adjusted to 0.272 by either adding more buffer or solid angiotensin I. Based on a mMolar extintion coefficient of 1.31 at 275 nM, the final concentration in the assay was 0.2 mM angiotensin I which is about 4–5 times the Km of this enzyme previously measured. Two hundred forty μl of the angiotensin I solution were added to each tube, then warmed to 37° C. Then μl of serum were added to each tube, sealed and incubated for 1 hour. Blank reaction mixtures containing 240 μl angiotensin I solution were similarly incubated without serum. The reaction was stopped with 1.45 ml 0.28 M NaOH and 10 μl of serum were added to the blank. Standard histidyl-L-leucine (5.165 nmol in 240 μl) was incubated with 10 μl of each serum for 1 hour and the reaction terminated with 1.45 ml 0.28 M NaOH. An unincubated standard his-leu solution to which 1.45 ml of 0.28 M NaOH was added prior to the serum (10 μl) was also used. A blank consisting of 240 μl buffer and 10 μl serum to which 1.45 ml of 0.28 M NaOH was added was also used.

For fluorescence development, 100 μl of 2% o-phthaldialdehyde in methanol were added to each tube and mixed with a vortex mixer. Exactly 10 minutes later, the reaction was terminated by addition of 200 μl of 3 M HCl and the tube again thoroughly mixed. The HCl addition was accompanied by the precipitation of a presumptive protein-o-phthaldialdehyde complex which was removed by centrifugation for 10 minutes at 1000 g. The fluorescence was read in a 1 cm rectangular fluorescence cuvette in a Perkin-Elmer MPF-4 fluorimeter with a 4 mm entrance and 8 mm exit slit and a 7.5 V energy output between 30–90 minutes after the addition of HCl, during which time the fluorescence was stable. The excitation wavelength was 360 mm and the emission fluorescence wavelength was 500 mm.

Calculation of enzymatic activity in nmoles L-histidyl-L-leucine released/min/ml of serum was calculated as follows: Angiotensin converting enzyme activity, nmole his-leu released/min/ml serum =

$$\frac{5.166 \text{ nmoles his-leu (standard) } (1/0.01 \text{ ml}) \text{ (FI assay} - \text{FI assay blank)}}{60 \text{ min (FI standard} - \text{FI standard blank)}} =$$

$$\frac{8.6 \text{ nmoles (FI assay} - \text{FI assay blank)/ml/min}}{\text{(FI standard} - \text{FI standard blank)}}$$

In none of the methods reported in the accompanying disclosure was there significant conversion of the product histidyl-L-leucine to histidine and leucine so that an average of the incubated and unincubated standard was used to calculate the FI of the standard. In one sample of a patient tested, significant activity for histidyl-L-leucine peptidase was found in the patient's serum. For this patient, the activity of the angiotensin I converting enzyme using angiotensin I as the substrate could not be measured. It is pointed out that if significant his-leu peptidase activity is found, it may be determined and used to make an approximate correction for the angiotensin converting enzyme activity with angiotensin I as the substrate. One method of approximation which may be used if the his-leu peptidase activity is reasonably linear during the assay period is to use the average of the his-leu standard and the final value of his-leu after enzyme incubation as the his-leu standard for the angiotensin converting enzyme activity.

In the practices of this invention as disclosed hereinabove, emphasis has been placed on angiotensin I and hippuryl-L-distidyl-L-leucine as substrates for the angiotensin converting enzyme which yield L-histidyl-L-leucine which is then reacted with o-phthaldialdehyde to form the resulting fluorescent adduct of L-histidyl-L-leucine and o-phthaldialdehyde. Other substrates in addition to angiotensin I and hippuryl-L-histidyl-L-leucine and which yield L-histidyl-L-leucine in the presence of angiotensin converting enzyme are also usefully employed in the practices of this invention, the only requirement for such L-histidyl-L-leucine yielding substrates being that the remaining moiety or moieties of the substrate yielding L-histidyl-L-leucine in the presence of angiotensin converting enzyme does not or do not otherwise interfere with the overall testing procedure, such as the formation of the fluorescent o-phthaldialdehyde and L-histidyl-L-leucine adduct and with the spectrofluorimetric determination of the fluorescent adduct.

As will be apparent to those skilled in the art in the light of the foregoing disclosure, many modifications, alterations and substitutions are possible without departing from the spirit or scope thereof.

I claim:

1. A method for determining angiotensin converting enzyme in untreated human serum which comprises admixing said serum to be tested for angiotension converting enzyme with a substrate to yield L-histidyl-L-leucine in the presence of angiotension converting enzyme, said substrate being selected from the group consisting of angiotensin I and hippuryl-L-histidyl-L-leucine, said substrate being added until said serum comprises about 4% by volume of the admixture thereof with said substrate, adding o-phthaldialdehyde to the resulting admixture in the form of about a 2% solution thereof in an amount such that the concentration thereof is about 0.11% by weight thereof, thereby forming the fluorescent adduct of o-phthaldialdehyde and the resulting produced L-histidyl-L-leucine and spectrofluorimetrically determining the amount of said fluorescent adduct.

2. A method in accordance with claim 1 wherein said substrate is hippuryl-L-histidyl-L-leucine, said hippuryl-L-histidyl-L-leucine undergoing conversion in the resulting admixture in the presence of angiotensin converting enzyme to hippurate and L-histidyl-L-leucine.

3. A method in accordance with claim 1 wherein said substrate is angiotensin I, said angiotensin I undergoing conversion in the resulting admixture in the presence of angiotensin converting enzyme to angiotensin II and L-histidyl-L-leucine.

4. A method in accordance with claim 1 wherein said serum to be tested for angiotensin converting enzyme by admixing with said substrate has also admixed therewith a halide.

5. A method in accordance with claim 4 wherein said halide is a chloride.

6. A method in accordance with claim 4 wherein said halide is derived from sodium chloride.

7. A method in accordance with claim 1 wherein said serum is obtained from blood which was allowed to clot for about an hour at room temperature and centrifuged for about 10 minutes at about 900 g.

8. A method in accordance with claim 1 wherein the solvent for said o-phthaldialdehyde is methanol.

* * * * *

UNITED STATES PATENT AND TRADEMARK OFFICE
CERTIFICATE OF CORRECTION

PATENT NO. : 4,108,726
DATED : August 22, 1978
INVENTOR(S) : Emanuel Silverstein It is certified that error appears in the above-identified patent and that said Letters Patent are hereby corrected as shown below:

Column 7, line 13, "linarly" should read -- linearly --

Column 9, line 3, "Then" should read -- Ten --

Column 9, line 62, "-distidyl-" should read -- -histidyl- --

Signed and Sealed this

First Day of May 1979

[SEAL]

Attest:

RUTH C. MASON
Attesting Officer

DONALD W. BANNER
Commissioner of Patents and Trademarks